(12) United States Patent
Opperman

(10) Patent No.: US 10,238,373 B1
(45) Date of Patent: Mar. 26, 2019

(54) RETRACTOR

(71) Applicant: David A. Opperman, Littleton, CO (US)

(72) Inventor: David A. Opperman, Littleton, CO (US)

(73) Assignee: COLORADO VOICE CLINIC, P.C., Denver, CO (US)

( * ) Notice: Subject to any disclaimer, the term of this patent is extended or adjusted under 35 U.S.C. 154(b) by 186 days.

(21) Appl. No.: 15/457,404

(22) Filed: Mar. 13, 2017

Related U.S. Application Data

(60) Provisional application No. 62/307,333, filed on Mar. 11, 2016.

(51) Int. Cl.
*A61B 17/02* (2006.01)
*A61B 1/24* (2006.01)

(52) U.S. Cl.
CPC ............... *A61B 17/02* (2013.01); *A61B 1/24* (2013.01)

(58) Field of Classification Search
CPC ............................. A61B 1/267; A61B 1/2673
USPC .................................................. 600/185–199
See application file for complete search history.

(56) References Cited

U.S. PATENT DOCUMENTS

| | | | | |
|---|---|---|---|---|
| 4,306,547 A * | 12/1981 | Lowell | ................... | A61B 1/267 128/200.26 |
| 4,384,570 A | 5/1983 | Roberts | | |
| 4,832,020 A * | 5/1989 | Augustine | ......... | A61M 16/0488 128/207.14 |
| 4,982,729 A * | 1/1991 | Wu | ......................... | A61B 1/07 128/200.26 |
| 5,065,738 A * | 11/1991 | Van Dam | ........... | A61B 1/00142 600/185 |
| 5,092,314 A * | 3/1992 | Zeitels | ................... | A61B 1/267 600/194 |
| 5,261,392 A * | 11/1993 | Wu | ........................ | A61B 1/267 128/200.26 |
| 5,776,053 A * | 7/1998 | Dragisic | ................ | A61B 1/267 600/195 |
| 5,893,830 A * | 4/1999 | Zeitels | ................... | A61B 1/267 600/185 |
| 6,652,453 B2 * | 11/2003 | Smith | ................ | A61B 1/00052 600/188 |
| 6,955,645 B1 * | 10/2005 | Zeitels | ...................... | A61B 1/24 600/187 |
| 7,946,981 B1 * | 5/2011 | Cubb | .................. | A61B 1/00052 600/120 |
| 8,495,999 B2 * | 7/2013 | Law | .................. | A61M 16/0488 128/200.26 |
| 8,721,535 B2 * | 5/2014 | Chen | ...................... | A61B 1/267 600/188 |

(Continued)

OTHER PUBLICATIONS

Olympus FK-WO TORS Laryngo-pharyngoscope retractor. http://olympusmedical.com.sg/products/all-products/instruments/ent-instruments/fk-wo-tors-laryngo-pharyngoscope-retractor/index.html. Retrieved from the internet Mar. 2016. 3 pages.

*Primary Examiner* — Eric S Gibson
(74) *Attorney, Agent, or Firm* — Lewis Brisbois Bisgaard & Smith LLP; Craig W. Mueller

(57) ABSTRACT

A retractor used in inner-oral surgery is provided that includes a maxilla portion configured to maintain a patient's mount in an open state. The retractor also includes a blade that maintains the position of the tongue so that surgical tools are not obstructed. The maxilla portion of one embodiment only extends a portion of the length of the blade.

6 Claims, 6 Drawing Sheets

(56) References Cited

U.S. PATENT DOCUMENTS

| | | | |
|---|---|---|---|
| 2009/0318768 A1* | 12/2009 | Tenger | A61B 1/0676 600/194 |
| 2010/0298644 A1* | 11/2010 | Kleene | A61B 1/2676 600/188 |
| 2011/0178372 A1* | 7/2011 | Pacey | A61B 1/00142 600/188 |
| 2011/0306839 A1* | 12/2011 | Young | A61B 1/00052 600/188 |
| 2012/0095295 A1* | 4/2012 | McGrath | A61B 1/267 600/194 |
| 2013/0237763 A1* | 9/2013 | Qiu | A61M 16/0488 600/188 |
| 2014/0336466 A1* | 11/2014 | Young | A61B 1/267 600/186 |
| 2015/0173598 A1* | 6/2015 | Alexander | A61B 1/00154 600/187 |

* cited by examiner

RETRACTOR

This application claims the benefit of U.S. Patent Provisional Patent Application Ser. No. 62/307,333, filed Mar. 11, 2016, the entire disclosure of which is incorporated by reference herein.

FIELD OF THE INVENTION

Embodiments of the present invention are generally related to retractors used with laryngoscopes. More specifically, one embodiment of the present invention is a retractor supported by a gallows laryngoscope holder that facilitates the use of traditional or robotic medical instruments.

BACKGROUND OF THE INVENTION

Laryngoscopes are routinely used to facilitate endotracheal intubation of patients, to provide an air passage for administration of anesthesia, and/or to establish an airway. In addition, laryngoscopes are commonly used in surgery to displace pharyngeal tissues to permit direct inspection of the larynx (i.e. direct laryngoscopy). Many laryngoscopes are L-shaped having a handle connected to single curved or straight blade. Otolaryngologists typically use a tubed laryngoscope to view the larynx and operate endoscopically on the true vocal cords (i.e. glottis). U.S. Pat. Nos. 4,384,570 and 5,092,314, which are incorporated by reference herein, discuss common laryngoscopes.

Laryngoscopes are often used with gallows-type holders that suspend a tubular retractor that receives traditional or robotic surgical instruments. The gallows holder and retractor support the patient's head and provides a clear path for traditional or robotic instruments to reach the larynx.

Alternatively, laryngoscopes are used, albeit less effectively, with jaw spreaders where mouth and larynx tissue are moved by various retractors interconnected to a peripheral structure positioned about the patient's head. One of the retractors interconnected to the peripheral structure is a non-cylindrical blade designed to hold the tongue in an ideal location. One drawback of using jaw spreaders, for example, those manufactured by Olympus® under the trade name FK-WO TORS, is that the retractors used are ineffective for endolaryngial surgery.

Thus, there is a long-felt need to provide a retractor for endolarynginal surgeries that effectively moves and maintains laryngidal tissue so the traditional or robotic surgical instruments can be used.

SUMMARY OF THE INVENTION

It is one aspect of embodiments of the present invention to provide a retractor for use with laryngoscopes. The contemplated retractor can accommodate traditional or robotic medical instruments.

It is another aspect of embodiments of the present invention to provide a retractor with a maxilla portion for contact with a patient's upper teeth that is shorter than a blade adapted to restrain the patient's tongue. The maxilla portion and the blade are curved in such a way to provide a generally cylindrical passage for the receipt of traditional or robotic medical instruments.

It is yet another aspect of embodiments of the present invention to provide a retractor adapted for use with a laryngoscope, comprising: a blade having a proximal end and a distal end; a handle interconnected to the proximal end of the blade; a maxilla portion interconnected to the blade, wherein the maxilla portion and the blade are curved to provide a generally cylindrical passage adapted to selectively receive a medical instrument; and wherein the maxilla portion is shorter than the blade.

It is still yet another aspect of embodiments of the present invention to provide a retractor adapted for use with a laryngoscope, comprising: a blade having a proximal end and a distal end; a handle interconnected to the proximal end of the blade; a maxilla portion interconnected to the blade, wherein the maxilla portion and the blade are curved to provide a generally cylindrical passage adapted to selectively receive a medical instrument; wherein the maxilla portion is shorter than the blade. wherein the maxilla portion has a first lateral edge and a second lateral edge that are interconnected to a lateral edge of the blade, the maxilla portion also comprising an arcuate surface that extends from the first lateral edge to the second lateral edge, and wherein the arcuate surface includes an outer portion that has a longitudinal dimension that is greater than the length of the first lateral edge and the second lateral edge; wherein the ends of the first lateral edge and the second lateral edge are spaced from the proximal end, and wherein the lateral edge of the blade and the outer portion of the arcuate surface define a c-shaped proximal edge of the maxilla portion; wherein the distal end is spaced transversely from the proximal end, and wherein the blade is curved; wherein the proximal end defines a longitudinal axis of the blade, and wherein the blade comprises a curved profile about the longitudinal axis; wherein the distal end has a tapered shape; and wherein the maxilla provides and opening and a passageway that is adapted to accommodate a surgical instrument.

The Summary of the Invention is neither intended nor should it be construed as being representative of the full extent and scope of the present invention. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

Figure 1:
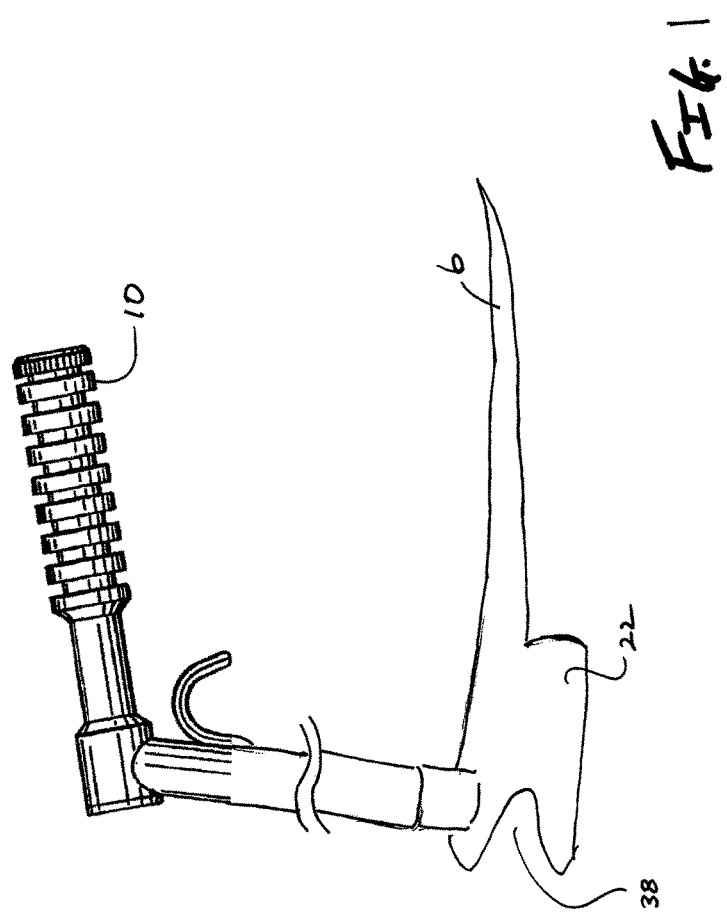
FIG. 1 is a front elevation view of the retractor of one embodiment of the present invention.
Figure 2:
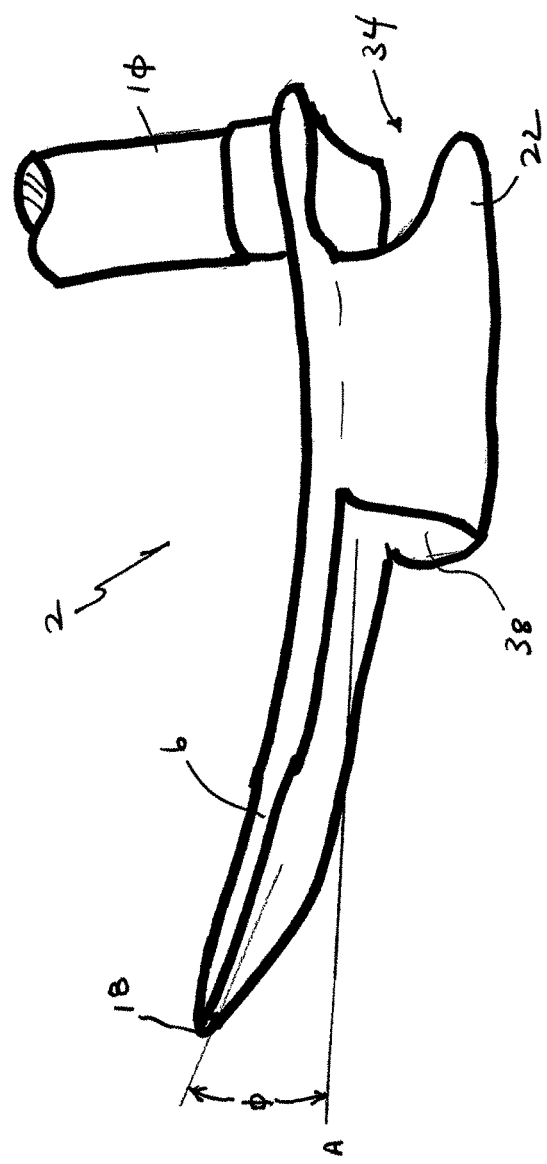
FIG. 2 is a detailed right perspective view of the retractor shown in FIG. 1.
Figure 3:
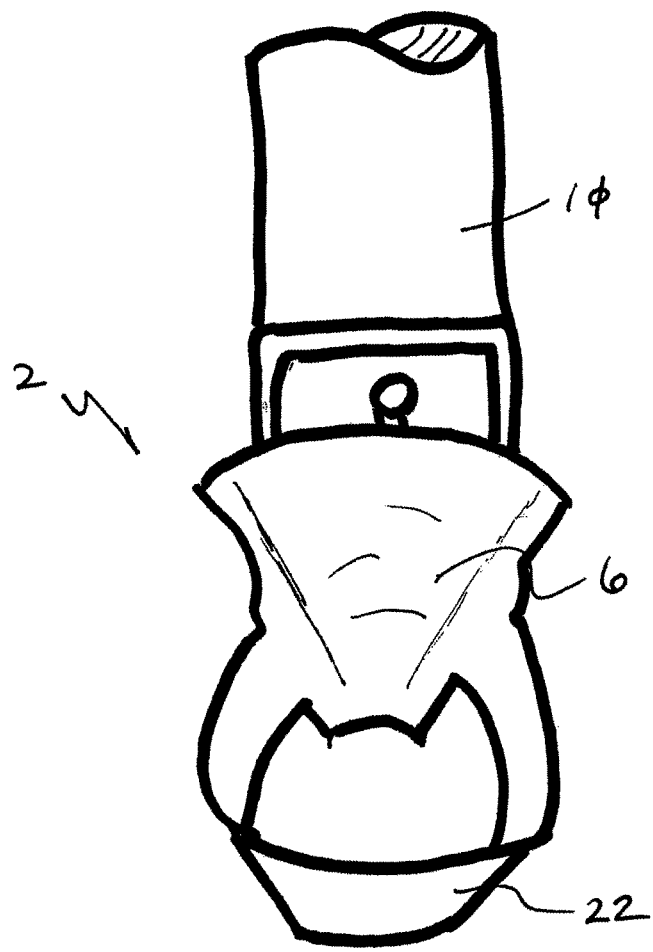
FIG. 3 is a detailed left elevation view of the retractor shown in FIG. 1.
Figure 4:
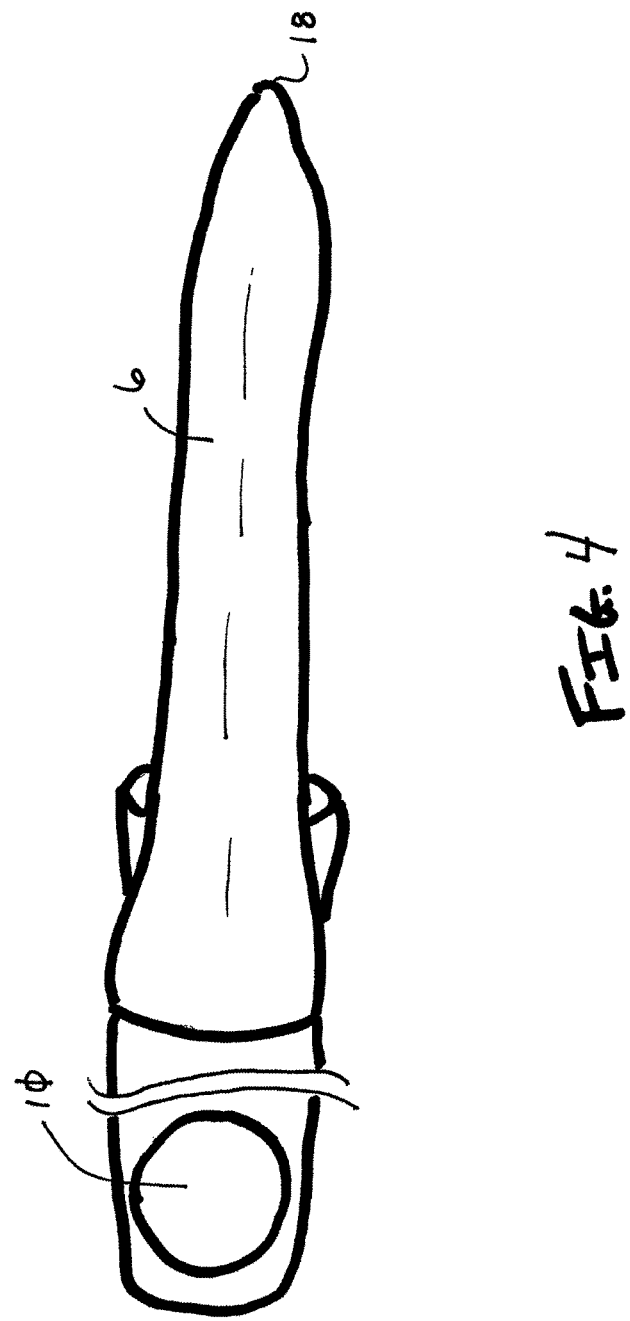
FIG. 4 is a top elevation view of FIG. 2.
Figure 5:
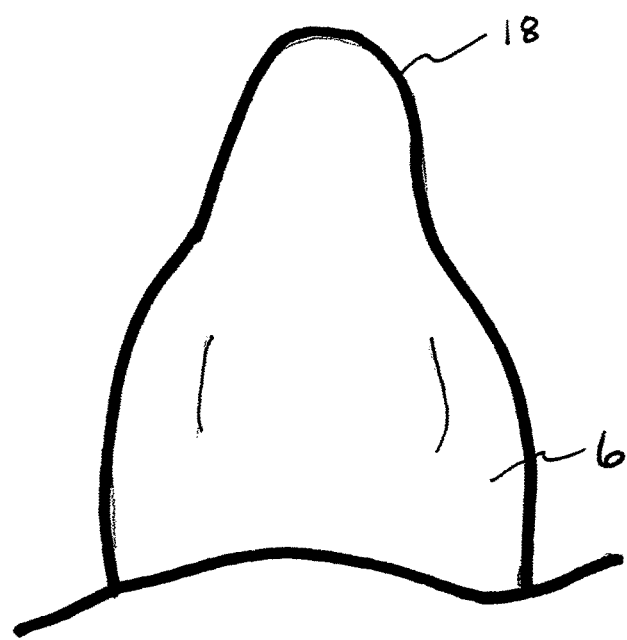
FIG. 5 is a detailed view of FIG. 4.

It should be understood that the drawings are not necessarily to scale. In certain instances, details not necessary for an understanding of the invention or that render other details difficult to perceive may have been omitted. It should be understood, of course, that the invention is not necessarily limited to the particular embodiments illustrated herein.

DETAILED DESCRIPTION

FIGS. 1-5 show the retractor 2 of one embodiment of the present invention that includes a blade 6 interconnected to a handle 10 that selectively interfaces with a gallows support 14. The blade 6 is curved about its longitudinal axis (A) to provide a semi-cylindrical profile. The blade 6 is also curved at the tip 18 at an angle ($\phi$) relative to the longitudinal axis of the retractor 2. The retractor includes a maxilla portion 22 configured to maintain a patient's 26 mouth open, while the blade 6 keeps the patient's tongue 30 away from the roof of the mouth. The maxilla portion 22 is generally cylindrical, thereby providing an opening 34 and a passage 38 that receive and accommodate surgical instruments.

In operation, the handle 10 is positioned outside the patient's mouth and the blade 6 is positioned in such a way to ensure a clear path to the patient's oral cavity and, thus, the pharynx, larynx, and associated structures.

The tip 18 of one embodiment of the present invention is tapered, which facilitates use of robotic medical instruments.

Figure 6:
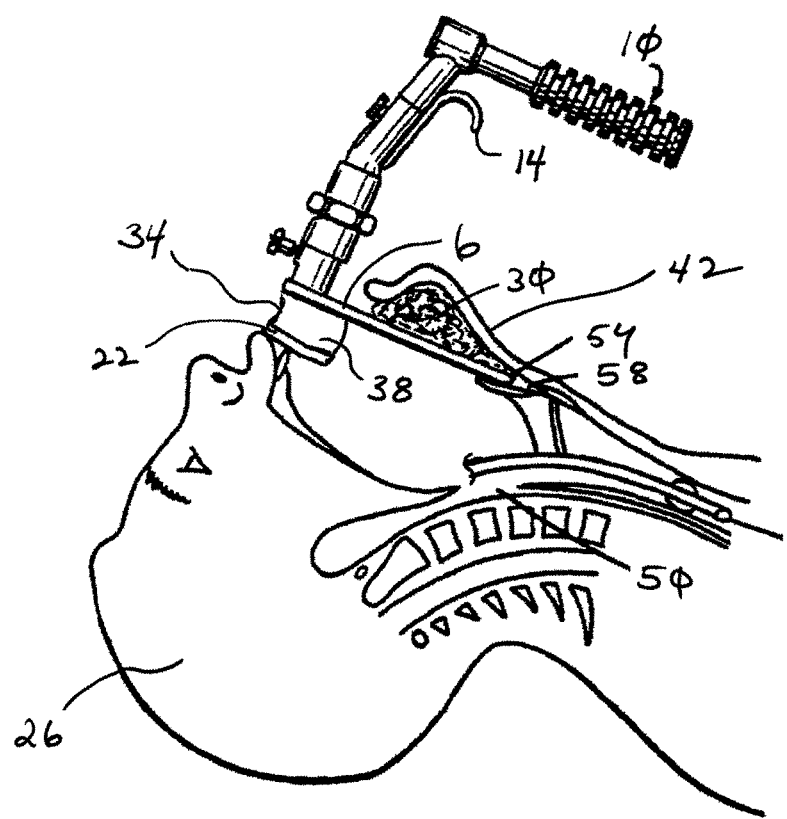
FIG. 6 is an elevation view of the retractor of one embodiment of the present invention positioned in a patient's mouth.

FIG. 6 shows the retractor 2 of one embodiment of the present invention provided in a patient's mouth. As one of ordinary skill in the art will appreciate, the maxilla portion 22 maintains the position of the patient's maxilla 42 (i.e., lower jaw). The blade 6 is positioned to maintain the patient's tongue 30 so a clear passage to the patient's pharynx 50, epiglottis 54, vallecula, 58, etc. is provided to the surgeon.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A retractor adapted for use with a laryngoscope, comprising:

a blade having a proximal end and a distal end that define a first length, the blade being adapted to constrain at least a portion of a patient's tongue;

a handle interconnected to the proximal end of the blade;

a maxilla portion interconnected to the blade, the maxilla portion having a distal end spaced from the proximal end of the blade;

wherein the maxilla portion and the blade are curved to provide a generally cylindrical passage that defines a longitudinal axis of the retractor, the cylindrical passage adapted to selectively receive a medical instrument; and wherein the distal end of the maxilla portion is closer to the proximal end of the blade than the distal end of the blade, such that a majority of the blade is exposed.

2. The retractor of claim 1, wherein the maxilla portion has a first lateral edge and a second lateral edge that are interconnected to corresponding lateral edges of the blade, wherein a proximal end of the first lateral edge and a proximal end of the second lateral edge are spaced from the proximal end of the blade, wherein the maxilla portion comprises an arcuate surface that extends from the first lateral edge to the second lateral edge, and wherein the arcuate surface includes an outer portion that has a longitudinal dimension greater than a length of the first lateral edge and the second lateral edge, the outer portion having a proximal end that generally corresponds with the proximal end of the blade.

3. The retractor of claim 2, wherein the lateral edge of the blade and the outer portion of the arcuate surface define a c-shaped proximal edge of the maxilla portion.

4. The retractor of claim 1, wherein the distal end of the blade is spaced transversely from the longitudinal axis of the retractor.

5. The retractor of claim 1, wherein the distal end has a tapered shape.

6. A retractor adapted for use with a laryngoscope, comprising:

a blade having a proximal end and a distal end;

a maxilla portion interconnected to the blade, wherein the maxilla portion and the blade are curved to provide a generally cylindrical passage that defines a longitudinal axis of the retractor;

wherein the maxilla portion is shorter than the blade;

wherein the maxilla portion has a first lateral edge and a second lateral edge that are interconnected to corresponding lateral edges of the blade, wherein proximal ends of the first and second lateral edges are spaced from the proximal end of the blade, the maxilla portion further comprised of an arcuate surface that extends from the first lateral edge to the second lateral edge, the arcuate surface including an outer portion that has a longitudinal dimension that is greater than a length of the first lateral edge and the second lateral edge;

wherein the lateral edge of the blade and the outer portion of the arcuate surface define a c-shaped proximal edge of the maxilla portion;

wherein the distal end of the blade is spaced transversely from the longitudinal axis of the retractor; and wherein the distal end of the blade has a tapered shape.

* * * * *